US010820810B2

(12) United States Patent
Saalasti et al.

(10) Patent No.: US 10,820,810 B2
(45) Date of Patent: Nov. 3, 2020

(54) METHOD AND A SYSTEM FOR DETERMINING THE MAXIMUM HEART RATE OF A USER OF IN A FREELY PERFORMED PHYSICAL EXERCISE

(71) Applicant: Firstbeat Analytics Oy, Jyväskylä (FI)

(72) Inventors: Sami Saalasti, Jyväskylä (FI); Aki Pulkkinen, Jyväskylä (FI); Tero Myllymäki, Jyväskylä (FI); Mikko Seppänen, Jyväskylä (FI); Kaisa Hämäläinen, Jyväskylä (FI); Maunu Toiviainen, Jyväskylä (FI); Tuukka Ruhanen, Jyväskylä (FI)

(73) Assignee: Firstbeat Analytics, Oy (FI)

( * ) Notice: Subject to any disclaimer, the term of this patent is extended or adjusted under 35 U.S.C. 154(b) by 0 days.

(21) Appl. No.: 16/691,781

(22) Filed: Nov. 22, 2019

(65) Prior Publication Data

US 2020/0163556 A1 May 28, 2020

(30) Foreign Application Priority Data

Nov. 26, 2018 (FI) ..................................... 20186002

(51) Int. Cl.
*A61B 5/0205* (2006.01)
*G16H 20/30* (2018.01)
(Continued)

(52) U.S. Cl.
CPC .......... *A61B 5/0205* (2013.01); *A61B 5/4884* (2013.01); *A61B 5/7278* (2013.01);
(Continued)

(58) Field of Classification Search
CPC ..... A61B 5/0205; A61B 5/024; A61B 5/0816; A61B 5/4884; A61B 5/7278; G16H 20/30
(Continued)

(56) References Cited

U.S. PATENT DOCUMENTS

2007/0032733 A1* 2/2007 Burton ............... A61B 5/02405
600/509
2011/0040193 A1 2/2011 Seppanen et al.
(Continued)

FOREIGN PATENT DOCUMENTS

WO 2017/117183 A1 7/2017

OTHER PUBLICATIONS

Finnish Office Action and Search Report dated May 27, 2019 in corresponding Finnish Application No. 20186002; 8 pages.
(Continued)

*Primary Examiner* — Christopher A Flory
(74) *Attorney, Agent, or Firm* — Samuel M. Korte; Max M. Ali (57) ABSTRACT

A method and a system for determining the maximum heart rate of a user in a freely performed physical exercise and using an apparatus with software and memory. An intensity model takes account of, in addition to heart rate, respiration rate and/or kinetics-information. The kinetics information depicts change in excess post-exercise oxygen consumption (EPOC), more generally the direction of cumulative physiological disturbance in homeostasis, whether it is at steady state, on-response (rising) or off-response (descending) to decrease the value of the determined maximal heart rate to obtain a result.

16 Claims, 5 Drawing Sheets

(51) Int. Cl.
*A61B 5/00* (2006.01)
*A61B 5/024* (2006.01)
*A61B 5/08* (2006.01)

(52) U.S. Cl.
CPC .............. *G16H 20/30* (2018.01); *A61B 5/024* (2013.01); *A61B 5/0816* (2013.01)

(58) Field of Classification Search
USPC .................................................. 600/300, 301
See application file for complete search history.

(56) References Cited

U.S. PATENT DOCUMENTS

| | | | | |
|---|---|---|---|---|
| 2012/0245439 | A1* | 9/2012 | Andre | A61B 5/0022 600/310 |
| 2013/0171599 | A1* | 7/2013 | Bleich | A61B 5/0456 434/247 |
| 2013/0178335 | A1* | 7/2013 | Lin | A63B 71/06 482/8 |
| 2014/0088444 | A1* | 3/2014 | Saalasti | A61B 5/0205 600/484 |
| 2015/0088006 | A1 | 3/2015 | Rapoport et al. | |
| 2015/0245777 | A1* | 9/2015 | Della Torre | A61B 5/11 600/301 |
| 2017/0049334 | A1* | 2/2017 | Saalasti | A61B 5/222 |
| 2017/0143262 | A1* | 5/2017 | Kurunmaki | A61B 5/0255 |
| 2018/0020931 | A1* | 1/2018 | Shusterman | A61B 5/02055 600/483 |
| 2018/0220901 | A1* | 8/2018 | LeBoeuf | A61B 5/6831 |
| 2018/0353090 | A1* | 12/2018 | Munaretto | A61B 5/02125 |
| 2019/0009134 | A1* | 1/2019 | Battaglini | A63B 24/0062 |
| 2019/0029586 | A1* | 1/2019 | Saalasti | G06F 19/3481 |

OTHER PUBLICATIONS

Karavirta, L. et al. "Estimation of maximal heart rate using the relationship between heart rate variability and exercise intensity in 40-67 years old men". In: European Journal of Applied Physiology Springer-Verlag, May 2008, vol. 103, No. 1, pp. 25-32.

Search Report dated Feb. 3, 2020 in European Application No. 19211232.4; 5 pages.

Saalasti, Sami, "Neutral Networks for Heart Rate Time Series Analysis", Jyväskylä Studies in Computing 33, Dec. 31, 2003, 194 pages.

* cited by examiner

METHOD AND A SYSTEM FOR DETERMINING THE MAXIMUM HEART RATE OF A USER OF IN A FREELY PERFORMED PHYSICAL EXERCISE

FIELD

This invention relates to a method and a system for determining the maximum heart rate, called HRmax of a user of in a freely performed physical exercise and using an apparatus with software and memory means.

BACKGROUND

Prior art present plurality of methods based on regression analysis for determining maximum heart rate of user Maximum heart rate represents the highest heart rate (HR) an individual can achieve through physical effort, typically represented by a number of beats per minute (bpm). The maximum heart rate value can be used to make a variety of calculations, such as to determine a person's fitness level, energy expenditure, or to create appropriate training heart rate zones an athlete should exercise at to accomplish a specific exercise goal.

The most direct way to determine maximum heart rate is for a person to perform maximal exercise and measure their highest heart rate. In many cases, this is not an appropriate method as many people do not wish to perform such a strenuous test. For many others, such as seniors or those with medical conditions, performing such high-intensity tests may also be unsafe.

As an alternative, it is possible to estimate a person's maximum heart rate. There are many methods that currently exist to provide an estimation of maximum heart rate. Simple calculations may use a person's age, gender, activity level, or weight. Most of these calculations are unreliable and may produce large errors. For example, age is known to correlate negatively with maximum heart rate, so age-based models of estimating maximum heart rate are common, the most well-known one being 220−[age]. However, these formulas have problems with accuracy and large outliers can occur. This significantly reduces these formulas' usefulness.

Many methods are only able to update the maximal heart rate value upwards, meaning that once a maximal heart value is found, it is only updated if a higher one is detected. However, it is a well-known fact that maximal heart rate decreases with age. Thus, if the same wearable device is used by the same user over many years, it should be possible to update the maximal heart rate value downwards.

Because maximum heart rate is used in so many other physiological calculations, inaccuracy of this value will have significant effect on calculating anything else. For example, a 10-BPM error in maximum heart rate may increase the error of fitness level estimate by 50% (i.e., mean absolute percentage error (MAPE) increases from 5% to 7.5%).

Thus, there is a need for a method of accurately estimating maximum heart rate that does not require a person to perform a maximum effort exercise. Therefore, there remains a continuous need for a more accurate and universal method to estimating maximum heart rate.

SUMMARY

The aim of this invention is to achieve a new method for determining maximum heart rate of a user and avoid above defects of prior art.

In the first embodiment the intensity model takes, in addition of heart rate, account of respiration rate and/or kinetics-information. That kinetics information depicts change in excess post-exercise oxygen consumption (EPOC), more generally the direction of cumulative physiological disturbance in homeostasis, whether it is at steady state, on-response (rising) or off-response (descending).

Generally speaking it is disclosed a method, which minimizes the absolute value of the difference between simulated (external) intensity and physiological (internal) intensity as a function of maximal heart rate.

The claimed method is able to decrease the value of the determined maximal heart rate, which is necessary when aiming a fully realistic result among aging people and users in all levels.

In a useful embodiment process obtaining the value of HRmax comprises also calculation of its reliability inversely according to a magnitude of the minimum value.

In another embodiment the validation includes further steps of:
 calculating a weighted average floating value of all obtained values of HRmax and storing it, and
 comparing each calculated average floating value with the initial value of HRmax and an age based value of HRmax using a predetermined criterion to choose the final value of HRmax.

In another embodiment scanning is carried in two ranges locating upwards and downwards from a chosen starting value and the obtained value with a higher reliability from two obtained values from said ranges is chosen as a final value of HRmax.

A BRIEF DESCRIPTION OF THE FIGURES

Advantages of embodiments of the present disclosure will be apparent from the following detailed description of the exemplary embodiments. The following detailed description should be considered in conjunction with the accompanying figures in which.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Further, many of the embodiments described herein are described in terms of sequences of actions to be performed by, for example, elements of a computing device. It should be recognized by those skilled in the art that the various sequences of actions described herein can be performed by specific circuits (e.g. application specific integrated circuits (ASICs)) and/or by program instructions executed by at least one processor. Additionally, the sequence of actions described herein can be embodied entirely within any form of computer-readable storage medium such that execution of the sequence of actions enables at least one processor to perform the functionality described herein. Furthermore, the sequence of actions described herein can be embodied in a combination of hardware and software. Thus, the various aspects of the present invention may be embodied in a number of different forms, all of which have been contemplated to be within the scope of the claimed subject matter. In addition, for each of the embodiments described herein, the corresponding form of any such embodiment may be described herein as, for example, "a computer configured to" perform the described action.

Figure 1:
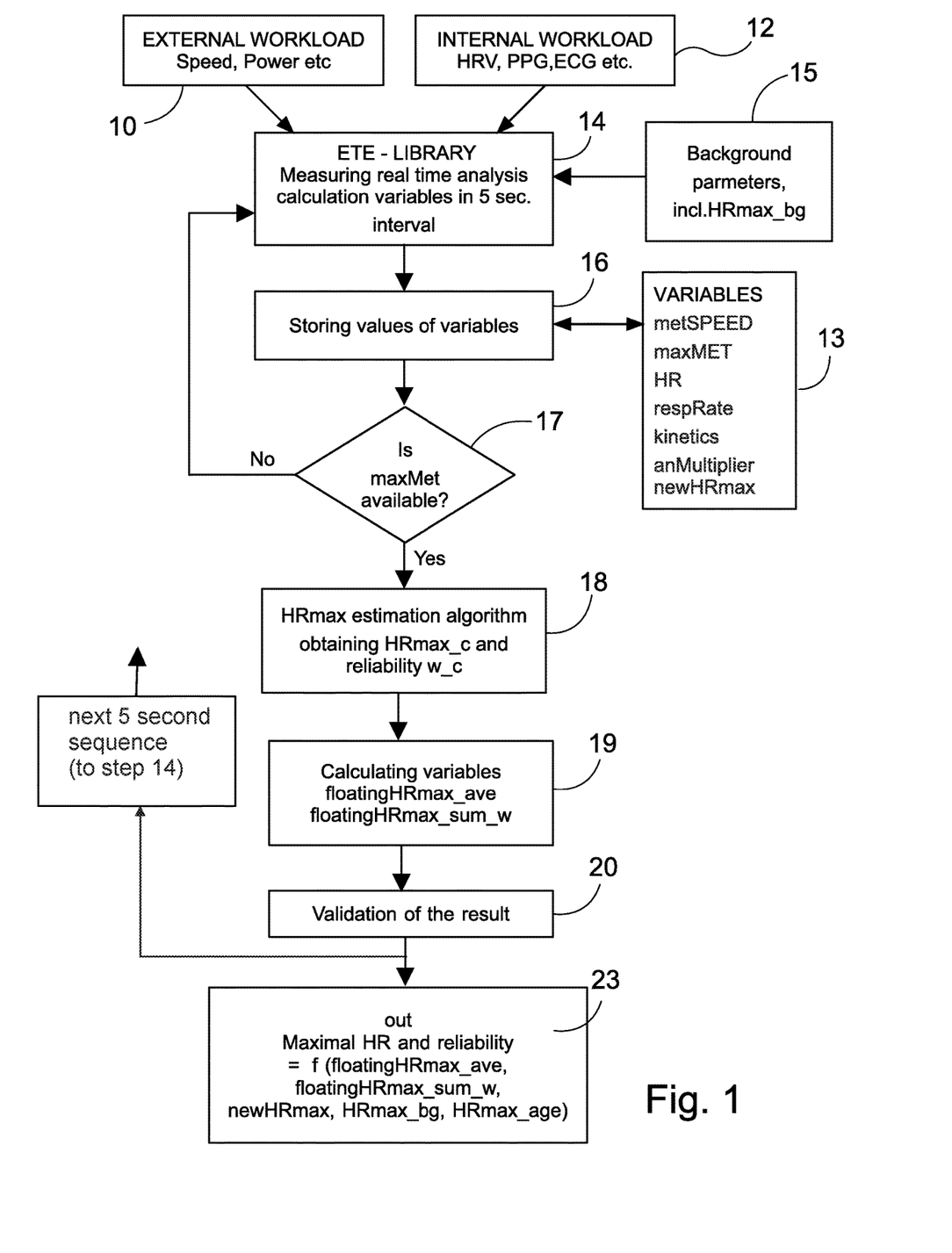
FIG. 1 presents an exemplary flowchart illustrating the main flow of execution of calculation of maximal heart rate (HRmax).
Figure 2:
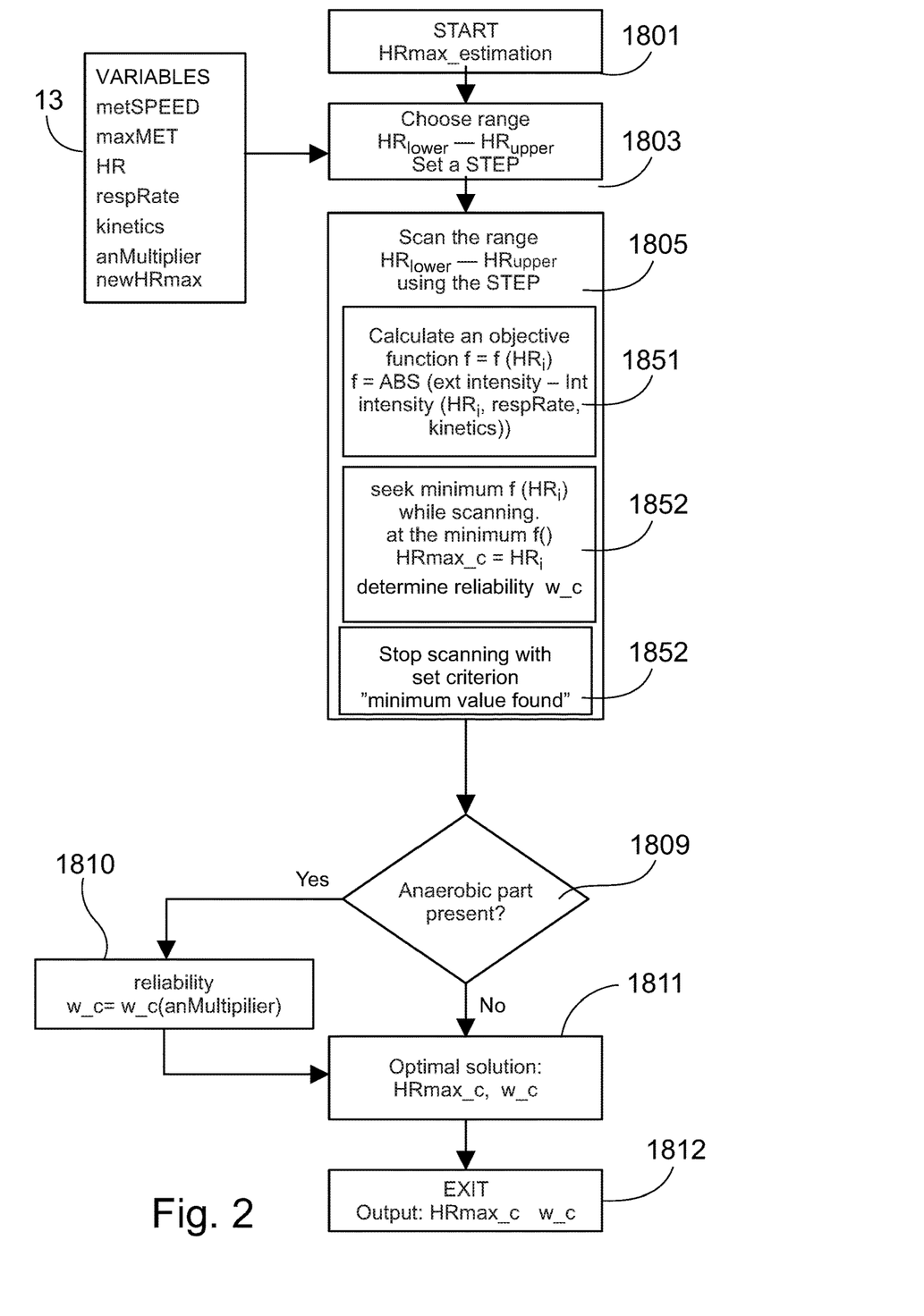
FIG. 2 presents the flowchart of the Estimation algorithm
Figure 3:
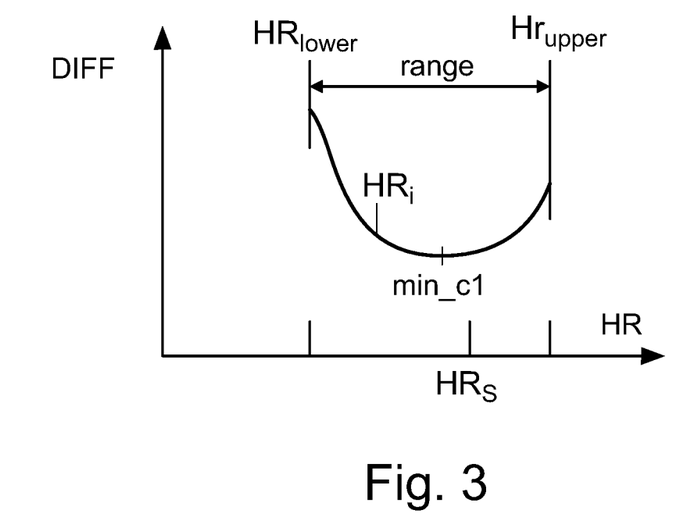
FIGS. 3 and 4 present exemplary diagrams depicting scanning the objective function in one or two ranges.
Figure 4:
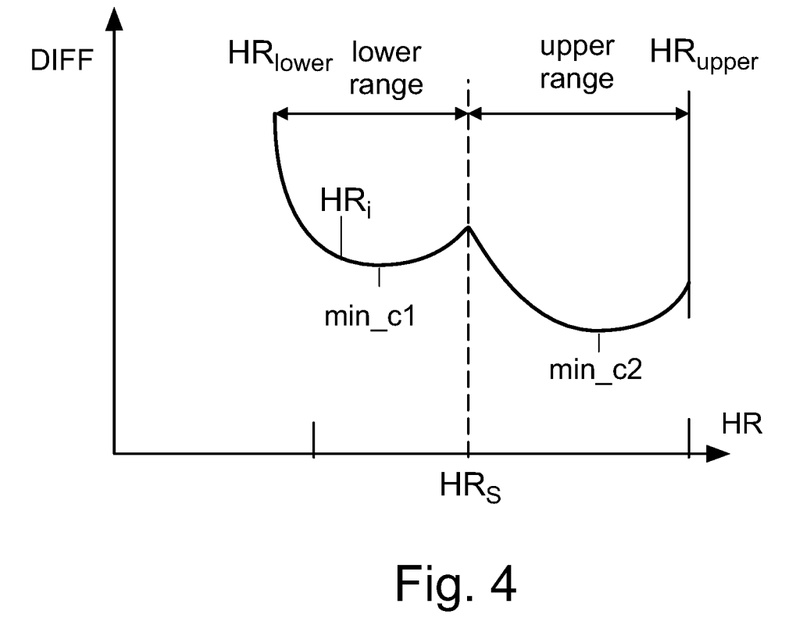

The method can be implemented in versatile devices, which have resources for measuring internal intensity and external workload, and run software to execute processes depicted in the exemplary flowcharts of FIGS. 1 and 2. A schematic hardware assembly is depicted below in exemplary FIG. 6.

Initial background and personal data may be stored. For example, the fitness level (for example VO2 max or METmax) and the maximum heart rate (HRmax), and the like, of the user may be stored. Personal data may be entered or determined beforehand.

Description of the Program (FIG. 1)

In FIG. 1 the shown calculation process of maximal heart rate (HRmax) may be a part of bigger software that monitors and analyzes physiology of a user. External (10) and internal (12) workloads are measured continuously. The external workload may be measured in many ways, for example (but not limited to) speed, altitude, power, etc. The internal workload is monitored usually by heart rate, which may be performed by various devices, such as (but not limited to) a heart rate belt, PPG- or ECG-device.

External and internal workloads are monitored (5 sec interval) by a host process, here embedded training effect (ETE)—library software, step 14. It will need here some background parameters, like age, sex, a possible initial value of HRmax, here $HRmax_{bg}$ from step 15. The ETE software calculates continuously several variables for HRmax estimation software. These variables are updated in every 5 seconds (more generally in 1-15 seconds) and stored temporarily (runtime), step 16.

Local Variables in this Function:

The core variables metSPEED, maxMET, HR, respRate, kinetics, anMultiplier are defined below.

Several other parameters are used:
w_c: reliability weight of the optimal solution (fixed point)
i: iteration index in while loop (integer)
f_old: previous value of the objective function (fixed point)
f_i: current value of the objective function (fixed point)
Int. Intensity_i: intensity (%-maxMET) at current solution (integer)

Output arguments in this function:
HRmax_c: optimal solution (integer)

The ETE library updates the (majority of) its global variables once every five seconds (more generally 1-15 seconds depending on a particular embodiment). Before estimating the maximal heart rate, the following variables are updated by ETE:

HR: current heart rate level (may be updated in principle after each heart beat)

speed: current walking/running speed of the user altitude: current altitude as obtained, e.g., via GPS or a barometer power: pedaling power (only available in the case of cycling or rowing)

inclination_angle: current angle of inclination (in radians) obtained directly or through sequential altitude and speed measurements metSpeed: MET estimate calculated using external workload, calculated as VO2/3.5 (where 3.5 is a constant), where VO2 is one of following (all in units: ml/min/kg):

$$VO2\_running=12.0*speed+3.5$$

$$VO2\_walking=4.3804*speed^2-0.2996*speed+7.0928$$

$$VO2\_power=(12.24*power+350.0)/weight$$

Here, speed is in units m/s. It is the raw input speed (without inclination correction). The weight of the user in kilograms is given by the variable weight.

In the case of running and walking, the inclination angle may be taken into account as follows:

If inclination angle is positive, as when going uphill:

$$VO2\_running=VO2\_running+speed*inclination\_angle*54.0$$

$$VO2\_walking=VO2\_walking+speed*inclination\_angle*108.0$$

There are similar equations available when the inclination angle is negative, as when going downhill.

In the case of running and walking, the software may select the minimum of these two values:
VO2=MIN(VO2_running, VO2_walking), when the type of exercise is not known.

In the case of cycling, only VO2_power is available, and this value is thus assigned to the variable VO2.

maxMET: the weighted maximal MET estimate given by the ETE library. Heart rate (beat-to beat interval and/or heart rate level) and external work (speed and optionally altitude, or pedaling/rowing power) are required for estimation of maxMET. If there has not been enough reliable data available during the current measurement (e.g., due to missing speed data or low-quality heart rate data), the maximal MET value given as background parameter is assigned to this variable. Otherwise the value of zero is used to indicate a missing value.

respRate: respiration rate (in Hz) estimated from the RRI sequence or heart rate data fxEpocHr: heart rate based EPOC estimate. This variable is used in the neural network that calculates the internal intensity (Int-int). The value of kinetics (selection of FIGS. 5A-5C) are defined by this variable.

anMultiplier: multiplier (greater than or equal to one) used to increase intensity based on anaerobic load.

floatingHRmax_ave: weighted average of maximal heart rate values given by the HRmax estimation algorithm (FIG. 2) during the current training session. The weights used in the calculation of the weighted average are the reliability weights (w_c, between zero and one), as described in FIG. 2. This variable is updated after the HRmax estimation algorithm in step 19. This variable is either initialized to zero in the beginning of the current exercise or the latest available value from the previous exercise session as the initial value.

floatingHRmax_sum_w: sum of the reliability weights (w_c) given by the HRmax estimation algorithm during the current training session. This variable is updated after the HRmax estimation algorithm in step 19. This variable is either initialized to zero in the beginning of the current exercise or the latest available value from the previous exercise session as the initial value.

newMaxHR: highest measured heart rate (i.e., largest value observed for the variable HR) encountered during the current training session The following internal (global) variables are calculated and stored in the initialization phase of the ETE library (in the beginning of the current training session) and they remain constant throughout the current training session (step 15):

age: age of the user in years weight: weight of the user in kilograms

HRmax_age: age-based estimate for maximal heart rate: 210−0.65*age

HRmax_bg: maximal heart rate given as background parameter; if this was not given by the user, the default value HRmax_age is assigned to it The maximal heart rate estimation algorithm (step 18) is run only if fitness level estimate (i.e., non-zero value for the variable maxMET) is available. The maximal heart rate estimation algorithm (step 18) minimizes the absolute difference between external and internal intensities as a function of maximal heart rate. The details of the algorithm with references to FIG. 2 are given later in the text.

After the estimation algorithm has finished with the optimal solution HRmax_c and its reliability weight w_c as outputs, a weighted average of HRmax solutions and the sum of reliability weights are updated with the following equations (step 19):

HRmax weighted average: floatingHRmax_ave=(floatingHRmax_ave+(w_c*HRmax_c)/floatingHRmax_sum_w)/(1+w_c/floatingHRmax_sum_w)

Sum of reliability weights: floatingHRmax_sum_w=floatingMaxHR_sum_w+w_c

With these floating weight values the obtained maximum heart rate estimate (HRmax_est) is validated and stored or rejected it based on a chosen criterion (step 20).

These two variables are updated after each call to the HRmax estimation routine (step 18). Optimal solutions (HRmax_c) with higher reliability weights (w_c) have larger effect on the value of the weighted average (floatingHRmax_ave).

The weighted average of optimal solutions floatingHRmax_ave provides an estimate for the maximal heart rate for the user. However, in the case of an erroneous input speed, altitude, power or heart rate data, the estimate may be unreliable. Hence, the estimate is validated (step 20) via comparing it with the values of the variables HRmax_bg, HRmax_age and newMaxHR. Then the execution returns to handle next 5 second sequence (to step 14). Also, the latest HRmax estimate is given as output every 5 seconds. Based on predetermined validation rules, the final maximal heart rate solution is calculated as a function of the variables floatingHRmax_ave, floatingHRmax_sum_w, HRmax_bg, HRmax_age and newMaxHR. The final solution and possibly a reliability calculated for it in the validation phase are given as output in step 23.

Description of the HRmax Estimation Algorithm
(FIG. 2)

The maximal heart rate estimation algorithm (step 18 and FIG. 2) is entered only if a non-zero value for maxMET is currently available.

The maximal heart rate estimation method tries to minimize the objective function f=f (HR_i) as a function of maximal heart rate, i.e., the decision variable HR_i (steps 1851 and 1852), where $$f(HR\_i)=|external\_intensity-internal\_intensity(HR\_i, HR, respRate, kinetics)|$$

The values of the variables external_intensity, HR, respRate and kinetics remain constant during the minimization (scanning) phase in each 5-second calculation round. Thus, only the second term internal_intensity( ) varies as the decision variable HR_i is changed during the optimization (scanning) process.

The external intensity is defined as the ratio of metSpeed and maxMET:

$$external\_intensity=metSpeed/maxMET$$

metSpeed and maxMET are the latest available values for the variables. They remain fixed during the scanning procedure of one calculation round.

Estimate for the internal intensity (a value in the range [0,1]) is provided by the HR based neural network model within the ETE library by the function internal_intensity( )(abbreviation: Int_int) which is a nonlinear function of the following variables:

relative heart rate: ratio between current heart rate (HR) and current candidate for maximal heart rate (HR_i): HR/HR_i respRate: respiration rate (in Hz) estimated from the RRI sequence or heart rate data kinetics: difference between the current and previous (5 s earlier) HR-based EPOC value: fxEpocHr(current)−fxEpocHr(previous)

Any model for the internal intensity should have as parameters at least relative heart rate (HR/HR_i) and one of said two parameters (respRate, kinetics)—preferably both parameters. An embodiment which has heart rate (HR/HR_i) as a sole parameter would also be possible but may suffer from inaccuracy.

Here, the objective function is thus the absolute value of the difference between the external and internal intensities. It should be noted that the function can also be, for example, the second power of the said difference, or any other function which monotonically increases in value as the absolute value of the difference between external and internal intensities increase.

The estimation algorithm (FIG. 2) uses the latest available values of the global variables (13). References are also made to FIGS. 3-5C.

The host software calls this child process (step 1801) and it defines a scanning range (step 1803) and sets a step (usually 1 bpm). In the scanning process (1805) heart rate HR_i runs stepwise across the range ($HR_{lower}$-$HR_{upper}$) from a set starting point. In each point the value of the objective function is calculated (step 1851) and it is compared to previous values (step 1852). Thus, the $n^{th}$ HR_i gets value from following equation: HR_n=$HR_{lower}$+n×STEP.

If there is only one range (FIG. 3), the starting point is somewhere near the background max heart rate (HRmax_bg). If there are two ranges (FIG. 4) and two scanning processes, both start preferably from the background max heart rate (HRmax_bg) and the lowest minimum value of two minimums defines the true minimum of objective function. Finally, the maximal heart rate value which leads to the lowest value for objective function is selected as HRmax candidate (variable HRmax_c in FIG. 2).

During scanning, the objective function f(HR_i) is calculated in each value of HR_i (step 1851). The other parameters are treated as constants during this 5 second process and they are picked up from list of the global variables (13). The optimization (scanning) process can be implemented by any numerical optimization method suitable for the task (e.g., linear scan, binary search, line search, etc.).

When the optimization of step 1852 is carried out using a linear scan using a running variable HR_i, the scanning process is stopped once all values in the range ($HR_{lower}$-$HR_{upper}$) has been scanned at the specified step size. The optimal solution (HRmax_c) is the value of the decision variable which produces lowest value for the objective function in this range. Alternatively, if the objective function may be assumed to contain a single minimum in the scanned range, the linear scan may be stopped early as soon as the first minimum has been found. Other search methods such as binary search and line search become applicable when such assumption on unimodality of the objective function may be assumed.

The maximal heart rate HR_max_c is the only decision variable in the minimization process. It should be noted that the external_intensity is dependent on maximal heart rate, as well: the estimation of the fitness level (maxMET) requires an estimate for maximal heart rate. However, based on empirical testing, the presented method converges towards correct solution even if value of the variable external_intensity is calculated using the maximal heart rate value given by the background variable HRmax_bg which remains constant throughout a single measurement. The presented method could be extended to the situation where the external_intensity depends on the running variable HR_i, i.e. on the decision variable HR_i, as well. However, it would increase the space and time complexity of the algorithm.

The reliability of the optimal solution (HRmax_c) is quantified with a non-negative reliability weight which correlates negatively with the value of the objective function at the optimal solution. In one example, a reliability weight is calculated with an empiric equation $w\_c=1$, if $0.2-5.3452 \times f(\ )>1$ $w\_c=0$, if $0.2-5.3452 \times f(\ )<0$ $w\_c=0.2-5.3452 \times f(\ )$ otherwise.

Here, the value of the objective function at the optimal solution is denoted with f( ).

Possible anaerobic part will be checked by steps 1809, 1810 and 1811 and it will decrease the weight (w_c) of the obtained optimal solution (maximum heart rate value HRmax_c). If significant anaerobic contribution is present during the current exercise, the anMultiplier variable has a value larger than one. When anaerobic contribution is not present, anMultiplier remains at 1.0.

If anMultiplier exceeds the value of 1.0, the value of the reliability weight w_c is decreased, e.g., with the following empirical equation:

$w\_c=w\_c/(2 \times an\text{Multiplier})$      (step 1810).

Finally, the optimal solution (HRmax_c) and its reliability weight (w_c) have been calculated (step 1811) and they are given as outputs in step 1812.

Figure 5A:
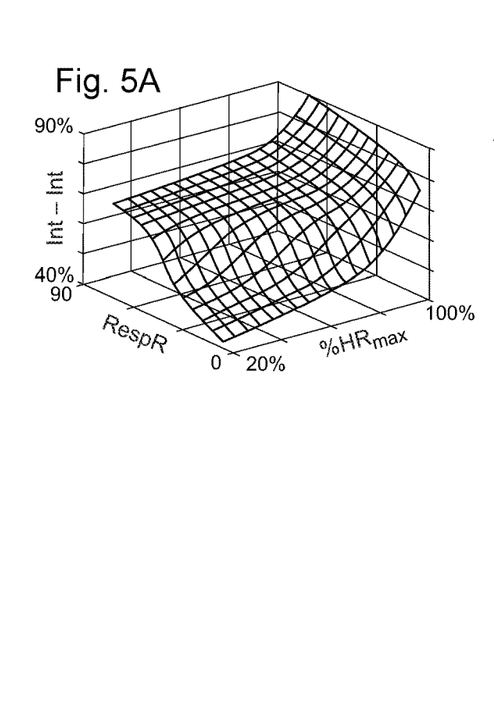
FIGS. 5A, 5B and 5C present exemplary charts for internal-intensity function "int-int"—used in the estimation algorithm during three typical exercise phases: A) steady state, B) on-response and C) off-response.
Figure 5B:
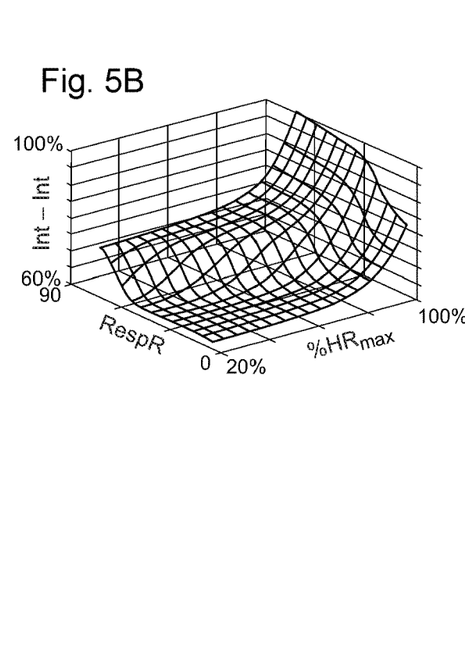
Figure 5C:
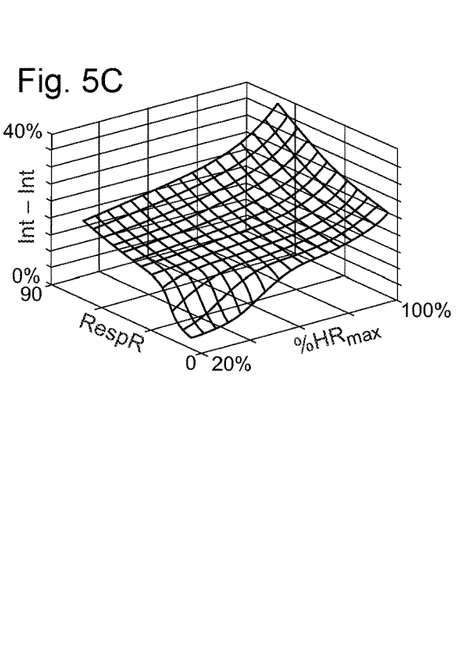

Description of the Internal Intensity Function (FIG. 5)

There are three separate situations (FIGS. 5A-5C), each of which defines the function used in the estimation algorithm during three typical exercise phases: A) steady state, B) one example of on-response and C) one example of off-response. These states A, B and C are referred to as "kinetics" and they are defined by EPOC-calculation or any other method determining a change in homeostasis. FIGS. 5B and 5C show just one example of both these states as the rate of change in fatigue accumulation or recovery and may vary, whereas steady-state (5A) always means a state where fatigue level remains completely unchanged.

Figure 6:
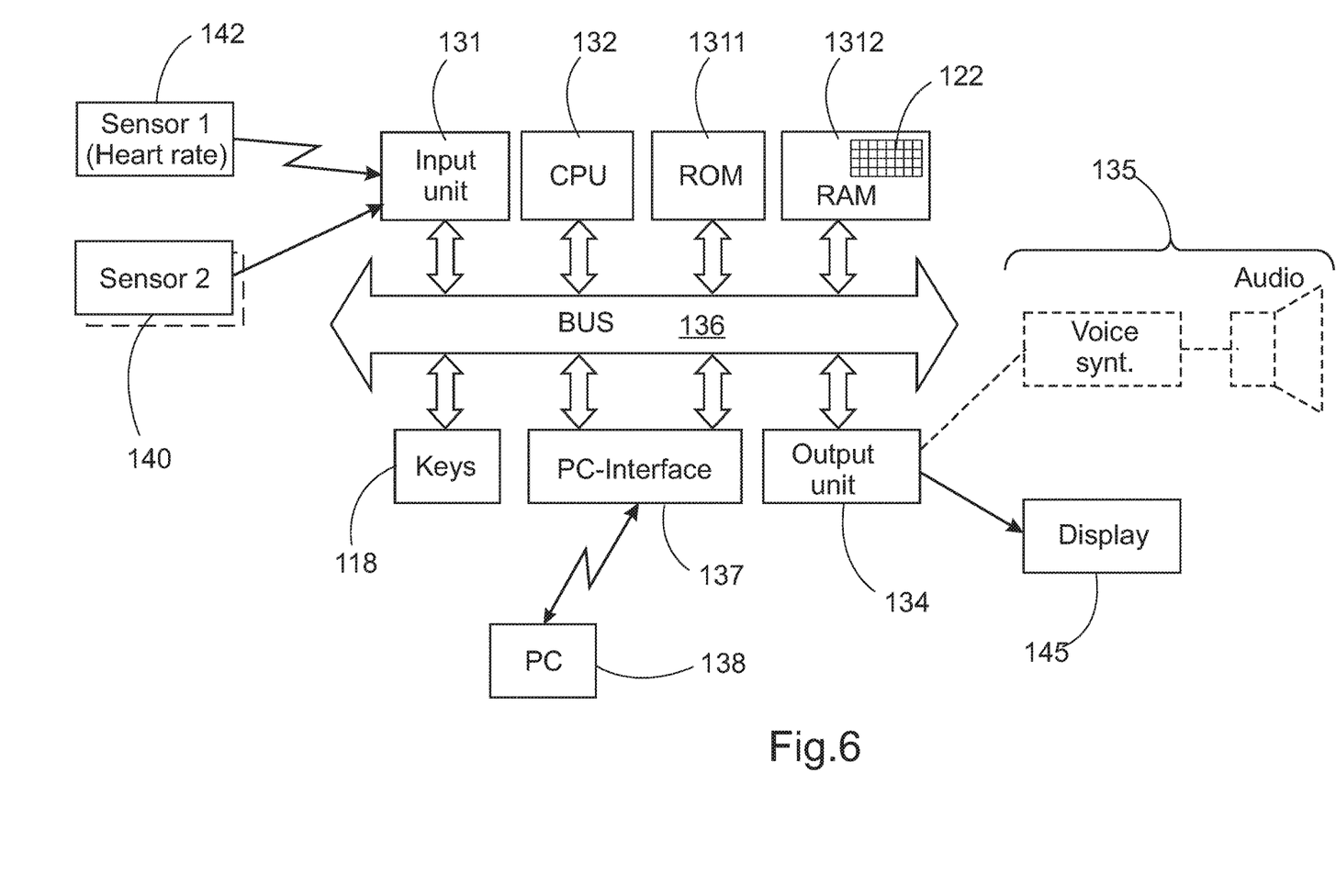
FIG. 6 presents an exemplary block diagram of a system with additional interfaces.

Description of Exemplary Embodiments (FIG. 6)

The system and method according to the exemplary embodiments can be applied in many kinds of devices as would be understood by a person of ordinary skill in the art. For example, a wrist top device with a heart-rate transmitter, a mobile device such as a phone, tablet or the like, or other system having CPU, memory and software therein may be used.

According to exemplary FIG. 6, in the implementation may include an assembly built around a central processing unit (CPU) 132. A bus 136 may transmit data between the central unit 132 and the other units. The input unit 131, ROM memory 1311, RAM memory 1312, keypad 118, PC connection 137, and output unit 134 may be connected to the bus. RAM memory has an allocated area 122 for HRmax calculation, namely local and global variables therein.

The system may include a data logger which can be connected to cloud service, or other storage as would be understood by a person of ordinary skill in the art. The data logger may measure, for example, physiological response and/or external workload.

A heart rate sensor 142 and any sensor 140 registering external workload may be connected to the input unit 131, which may handle the sensor's data traffic to the bus 136. In some exemplary embodiments, the PC may be connected to a PC connection 137. The output device, for example a display 145 or the like, may be connected to output unit 134. In some embodiments, voice feedback may be created with the aid of, for example, a voice synthesizer and a loudspeaker 135, instead of, or in addition to the feedback on the display. The sensor 140 which may measure external workload may include any number of sensors, which may be used together to define the external work done by the user.

More specifically the system presented in FIG. 6 may have the following parts for determining the maximum heart rate of a user.

a heart rate sensor (142) configured to measure the heartbeat of the person, the heart rate signal being representative of the heartbeat of the user;

at least one sensor (140) to measure an external workload during an exercise, and     a data processing unit (132) operably coupled to the said sensors (142, 140), a memory (1311, 1312) operably coupled to the data processing unit (132),     the memory may be configured to save background information of a user, for example, background data including an earlier fitness level, as well as HRmax and the like.

The data processing unit (132) may include dedicated software configured to execute the embodiments described in the present disclosure.

As described above in the exemplary embodiments, default values of the optional parameters may be stored in a ROM memory, in an EEPROM (Electrically Erasable Programmable Read-Only Memory) memory, or in other memory as would be understood by a person of ordinary skill in the art.

The invention claimed is:

1. A method for determining the maximum heart rate, called HRmax, of a user in a freely performed physical exercise and using an apparatus with software and memory means, comprising:

providing and storing an initial value for HRmax, providing and storing an intensity model of actual internal intensity (Int-int) utilizing at least relative heart rate and one of following: respiration rate, disturbance in homeostasis (Kinetics), the method comprising steps of:

continuously measuring heart rate (HR), by a heart rate sensor and recording a measured heart rate value at least temporarily, continuously measuring by at least one sensor an external workload, wherein a measured workload value is recorded at least temporarily and associated with the measured heart rate value continuously calculating values for several variables and updating them in memory using said software and memory means, said variables including a variable depicting current internal intensity using recorded values of heart rate (HR), and at least one of following two according to said intensity model:

a variable depicting current respiration rate called as respRate using recorded values of heart rate (HR), and/or a variable (kinetics) depicting at least direction of cumulative physiological disturbance in homeostasis using the recorded values of heart rate and external workload, and a variable depicting fitness level (maxMET), a variable depicting external intensity based on the recorded values of external workload (metSPEED) and fitness level, and the method including further steps of:

selecting a range for heart rate (HR_i) nearby the last recorded maximum heart rate (HRmax) and storing values $HR_{lower}$, $HR_{upper}$ for upper and lower ends of that range, seeking a minimum value of an objective function (f( )) depicting the difference between external intensity and internal intensity by scanning the objective function (f( )) across the range between the values $HR_{lower}$ $HR_{upper}$ using said intensity model having heart rate HR_i as a running variable therein, and obtaining and storing a maximum heart rate estimate (HRmax_est) at HR_i giving said minimum value, and validating and storing the obtained value of maximum heart rate estimate (HR_est) or rejecting it based on a chosen criterion.

2. The method according to claim 1, wherein said objective function f( ) is calculated using an equation:

$$f(HR\_i)=|external\_intensity-internal\_intensity(HR\_i, HR, respRate, kinetics)|, \text{where}$$

external_intensity=metSPEED/maxMET, and internal intensity is obtained from an intensity model "Int-int" having a running variable HR_i and values for heart rate HR, respiration rate respRate and kinetics as constants during scanning.

3. The method according to claim 1, wherein said obtaining the value of HRmax comprises also calculation of its reliability inversely according to a magnitude of the minimum value of the objective function.

4. The method according to claim 3, wherein said validation includes further steps of:

calculating a weighted average floating value of all obtained values of HRmax and storing it, and comparing the calculated average floating value with the initial value of HRmax and an age-based value of HRmax and predetermined criteria to choose the final value of HRmax.

5. The method according to claim 1, wherein said scanning is carried in two ranges locating upwards and downwards from a chosen starting value and the obtained value with a higher reliability from two obtained values from said ranges is chosen as a final value of HRmax.

6. The method according to claim 4, wherein said scanning is carried in two ranges locating upwards and downwards from a chosen starting value and the obtained value with a higher reliability from two obtained values from said ranges is chosen as a final value of HRmax.

7. The method according to claim 5, wherein local variables are updated every 1-15 seconds and stored temporarily.

8. The method according to claim 6, wherein local variables are updated every 1-15 seconds and stored temporarily.

9. The method according to claim 1, wherein the intensity model "int-int" has three input states: A—recovery, B—steady-state and C—accumulating fatigue, one of which is selected by a kinetics method determining a change in homeostasis and each having influence on internal intensity value.

10. The method according to claim 5, wherein the intensity model "int-int" has three input states: A—recovery, B—steady-state and C—accumulating fatigue one of which is selected by a kinetics method determining a change in homeostasis and each having influence on internal intensity value.

11. The method according to claim 6, wherein the intensity model "int-int" has three input states: A—recovery, B—steady-state and C—accumulating fatigue, one of which is selected by a kinetics method determining a change in homeostasis and each having influence on internal intensity value.

12. The method according to claim 10, wherein the kinetics method is defined by excess post-exercise oxygen consumption (EPOC)-calculation.

13. The method according to claim 1, wherein the chosen criteria to validate the obtained value of maximum heart rate estimate (HRmax_est) is a specific criterion using an age based and background HRmax values.

14. The method according to claim 6, wherein the chosen criteria to validate the obtained value of maximum heart rate estimate (HRmax_est) is a specific criterion using an age based and background HRmax values.

15. The method according to claim 13, wherein the chosen criteria to validate the obtained value of maximum heart rate estimate (HRmax_est) is a specific criterion using an age based and background HRmax values.

16. A system for determining the maximum heart rate, called HRmax of a user of in a freely performed physical exercise comprising an apparatus with software and memory means, the apparatus comprising:

means for providing initial value for HRmax storing that in the memory, memory for storing an intensity model (Int-int) of actual internal intensity relation at least heart rate, respiration rate and disturbance in homeostasis (kinetics), means for executing following steps of:

a heart rate sensor for continuously measuring heart rate (HR) and means for recording a measured heart rate value at least temporarily, at least one second sensor continuously measuring an external workload, and means for recording a respective value at least temporarily and associated the measured heart rate value means for continuously calculating values for several variables and updating them in memory using said software and memory means, said variables including a variable depicting current internal intensity called as % HRmax using recorded values of heart rate (HR), a variable depicting current respiration rate called as respRate using recorded values of heart rate (HR), a variable (kinetics) depicting at least direction of cumulative physiological disturbance in homeostasis using the recorded values of heart rate and external workload, a variable depicting fitness level (maxMET), a variable depicting external intensity using measured external workload external intensity using measured external workload and maxMET the apparatus having means to execute further steps of:

selecting a range for heart rate (HR_i) nearby the last recorded actual maximum heart rate (HRmax)

seeking a minimum value of an objective function f( )defined by an equation:

$$f(HR\_i)=|external\_intensity-internal\_intensity(HR\_i, HR, respRate, kinetics)|, where$$

external_intensity=metSPEED/maxMET, internal intensity is obtained from an intensity model "Int-int" having running variable HR_i and values for heart rate HR respiration rate respRate and kinetics as constants during scanning, obtaining and storing a maximum heart rate estimate (HRmax_est) at HR(i) giving said minimum value, and means for validating and storing the obtained value of HRmax or rejecting it based on a chosen criterion.

* * * * *